(12) United States Patent
Greenberg

(10) Patent No.: US 9,585,735 B2
(45) Date of Patent: Mar. 7, 2017

(54) LOCKING IMPLANT

(71) Applicant: WeRImplants Ltd., Rishon Lezion (IL)

(72) Inventor: Rodica Greenberg, Givataim (IL)

(73) Assignee: WeRImplants Ltd., Rishon Lezion (IL)

( * ) Notice: Subject to any disclaimer, the term of this patent is extended or adjusted under 35 U.S.C. 154(b) by 0 days.

(21) Appl. No.: 15/086,950

(22) Filed: Mar. 31, 2016

(65) Prior Publication Data
US 2016/0278886 A1 Sep. 29, 2016

Related U.S. Application Data

(63) Continuation-in-part of application No. 13/393,486, filed as application No. PCT/IL2010/000699 on Aug. 26, 2010, now abandoned.

(60) Provisional application No. 61/244,116, filed on Sep. 21, 2009.

(51) Int. Cl.
*A61C 13/12* (2006.01)
*A61C 8/00* (2006.01)

(52) U.S. Cl.
CPC .......... *A61C 8/0033* (2013.01); *A61C 8/0019* (2013.01); *A61C 8/0022* (2013.01); *A61C 8/0037* (2013.01); *A61C 8/0069* (2013.01); *A61C 8/0074* (2013.01); *A61F 2250/0067* (2013.01)

(58) Field of Classification Search
CPC .......................................... A61C 8/00–8/0098
USPC ................................................. 433/172–176
See application file for complete search history.

(56) References Cited

U.S. PATENT DOCUMENTS

| | | | | |
|---|---|---|---|---|
| 2,685,877 A * | 8/1954 | Dobelle | ................ | A61F 2/3603 411/21 |
| 5,013,242 A * | 5/1991 | Prezmecky | .......... | A61C 8/0033 433/173 |
| 5,141,435 A * | 8/1992 | Lillard | ................. | A61C 8/0033 433/176 |
| 5,890,902 A * | 4/1999 | Sapian | ................. | A61C 8/0048 433/173 |
| 6,004,088 A * | 12/1999 | Hunt | .................... | F16B 13/0808 411/21 |
| 8,540,513 B1 * | 9/2013 | Aldoukhi | ............. | A61C 8/0033 433/172 |
| 2010/0268175 A1 * | 10/2010 | Lunsford | ........... | A61B 17/3478 604/272 |

* cited by examiner

*Primary Examiner* — Yogesh Patel
(74) *Attorney, Agent, or Firm* — The IP Law Firm of Guy Levi, LLC

(57) ABSTRACT

The present disclosure is directed to an expanding bone implant and, more particularly to an oral implant having radially extendable anchoring means.

13 Claims, 3 Drawing Sheets

LOCKING IMPLANT

CROSS REFERENCE TO RELATED APPLICATIONS

The present application is a Continuation-in-part of pending U.S. application Ser. No. 13/393,486, filed May 11, 2012, which claims priority to, and the benefit of, PCT Application No. PCT/IL2010/00699 filed on now expired Aug. 26, 2010, both which are hereby incorporated herein by reference.

BACKGROUND

The present invention relates to an expandable bone implant and, more particularly to an oral implant having radially extendable anchoring means.

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the alveolar bone (i.e., jawbone or cortica) of a patient. The surgeon first accesses the alveolar bone through the patient's gum tissue and removes any remains of the tooth to be replaced. Next, the specific site in the alveolar bone where the implant will be anchored is prepared by drilling and/or reaming to accommodate the width/diameter of the dental implant to be inserted. Then, the dental implant is inserted into the hole, typically by screwing, although other techniques are known for introducing the implant in the jawbone.

After the implant is initially installed in the bone, a temporary healing cap/screw may be secured over the exposed proximal end in order to seal the internal bore of the implant. The patient's gums are then sutured over the implant to allow the implant site to heal and to allow desired osseointegration to occur. Complete osseointegration typically takes anywhere from three to ten months.

During stage II, the surgeon reaccesses the implant fixture by making an incision through the patient's gum tissues. The healing cap/screw is then removed, exposing the proximal end of the implant. Typically, an impression coping may be attached to the implant and a mold or impression is then taken of the patient's mouth to accurately record the exact position and orientation of the implant within the mouth. Stage II is typically completed by attaching to the implant a temporary healing abutment or other transmucosal component to control the healing and growth of the patient's gum tissue around the implant site. In a modified procedure, an abutment or other transmucosal component is either integrally formed with the implant or is attached to the implant during stage I. In such a procedure, stages I and II are effectively combined in to a single stage.

Stage III involves the fabrication and placement of cosmetic tooth prosthesis to the implant fixture. The plaster analogue provides laboratory technicians with a model of the patient's mouth, including the orientation of the implant fixture and/or abutment relative to the surrounding teeth. Based on this model, the technician constructs a final restoration. The final step in the restorative process is replacing the temporary healing abutment with the final abutment and attaching a final prosthesis to the final abutment.

The dental implant is typically fabricated from pure titanium or a titanium alloy and includes a body portion and a collar. The body portion is configured to extend into and osseointegrate with the alveolar bone. The top surface of the collar typically lies over, under, or flush with the crest of the jawbone bone. The final abutment typically lies on the top surface and extends through the soft tissue, which lies above the alveolar bone. As mentioned above, the abutment supports the final prostheses. Typically, the coronal or crown portion of the collar and the portions of the final abutment that extend through the soft tissue have machined- or polished surfaces. This is believed in the art to prevent the accumulation of plaque and calculus and facilitates cleaning.

Conventional dental implants that provide the foundation for a prosthetic tooth as described hereinabove require a substantially solid, dense bone in which to be inserted and/or installed and/or inlaid. If there is insufficient bone quantity, quality or density, for example soft and/or osteoporotic bone, conventional implants may suffer osseointegration failure, loosen and fail.

An expandable dental implant may comprise a screw which is torqued into a jacket having multiple deformable ends that expand into the surrounding bone; as exemplified by U.S. Pat. No. 6,332,778 (Choung), the contents of which is incorporated herein by reference in their entirety. The larger diameter provided by the expanded multiple ends, may aid in locking the implant in the osteoporotic bone.

BRIEF SUMMARY

Embodiments of the disclosed technology provide an implant assembly, more specifically, a dental implant assembly. One assembly includes a bladed dental implant assembly for securing in a jaw bone. The bladed dental implant assembly includes a body portion configured to be located within a bore in a jaw bone.

Accordingly, in an embodiment, provided herein is a bladed implant assembly for supporting a prosthesis, the assembly comprising: a monocoque implant having a proximal end and a distal end comprising: a threaded body portion located at a distal end of the monocoque implant; an abutment portion located distally to the body portion; a non-threaded portion located proximally to the threaded body portion; a cylindrical, conical, or frusto-conical proximal end, located proximally to the non-threaded portion; and a central bore extending through the monocoque implant body having a distal end and a concave proximal end, having an engagement portion and comprising two or more axially elongated openings radially disposed and extending through the non-threaded portion with one or more L-shaped resilient blades having an elongated distal member and a transverse proximal tab, the elongated distal member extending from the distal end of the axially elongated openings, each elongated distal member of each blade being a portion of the external surface of the non-threaded body portion and configured to move between a retracted position, whereby each of the L-shaped resilient blades radially extends into the central bore and an extended position, whereby each of the L-shaped resilient blades is flush with the external surface of the non-threaded body portion; and a shaft member comprising: a distal portion; and a detachable actuating proximal portion, wherein the actuating proximal portion includes a distal end having a flat surface and a proximal end having arcuate surface, corresponding to the concave surface of the proximal end of the central bore, said shaft member configured to engage the central bore thereby causing the actuating lower portion to radially extend one or more of each of the L-shaped resilient blades from the non-threaded body portion, anchoring the monocoque implant into bone structure surrounding the monocoque implant located proximally to the abutment portion.

In another embodiment, the invention provides a method for providing support for a dental prosthesis, the method comprising the steps of drilling and/or reaming an opening capable of accommodating a dental implant; inserting an implant assembly, the assembly comprising: a monocoque implant having a proximal end and a distal end comprising: a threaded body portion located at a distal end of the monocoque implant; an abutment portion located distally to the body portion; a non-threaded portion located proximally to the threaded body portion; a conical, or frusto-conical proximal end, located proximally to the non-threaded portion; and a central bore extending through the monocoque implant body having a distal end and a concave proximal end, having an engagement portion and comprising two or more axially elongated openings radially disposed and extending through the non-threaded portion with one or more L-shaped resilient blades having an elongated distal member and a transverse proximal tab, the elongated distal member extending from the distal end of the axially elongated openings, each elongated distal member of each blade being a portion of the external surface of the non-threaded body portion and configured to move between a retracted position, whereby each of the L-shaped resilient blades radially extends into the central bore and an extended position, whereby each of the L-shaped resilient blades is flush with the external surface of the non-threaded body portion; and a shaft member comprising: a distal portion; and a detachable actuating proximal portion, wherein the actuating proximal portion includes a distal end having a flat surface and a proximal end having arcuate surface, corresponding to the concave surface of the proximal end of the central bore, said shaft member configured to engage the central bore thereby causing the actuating lower portion to radially extend one or more of each of the L-shaped resilient blades from the non-threaded body portion, anchoring the monocoque implant into bone structure surrounding the monocoque implant located proximally to the abutment portion; and engaging the shaft member, thereby radially extending the blades and anchoring the dental implant into the bone structure surrounding the implant body portion thus providing support for a dental prosthesis.

These, additional, and/or other aspects and/or advantages of the oral implant having radially extendable anchoring means are set forth in the detailed description which follows; possibly inferable from the detailed description; and/or learnable by practice of the methods provided implementable in the assemblies described.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1:
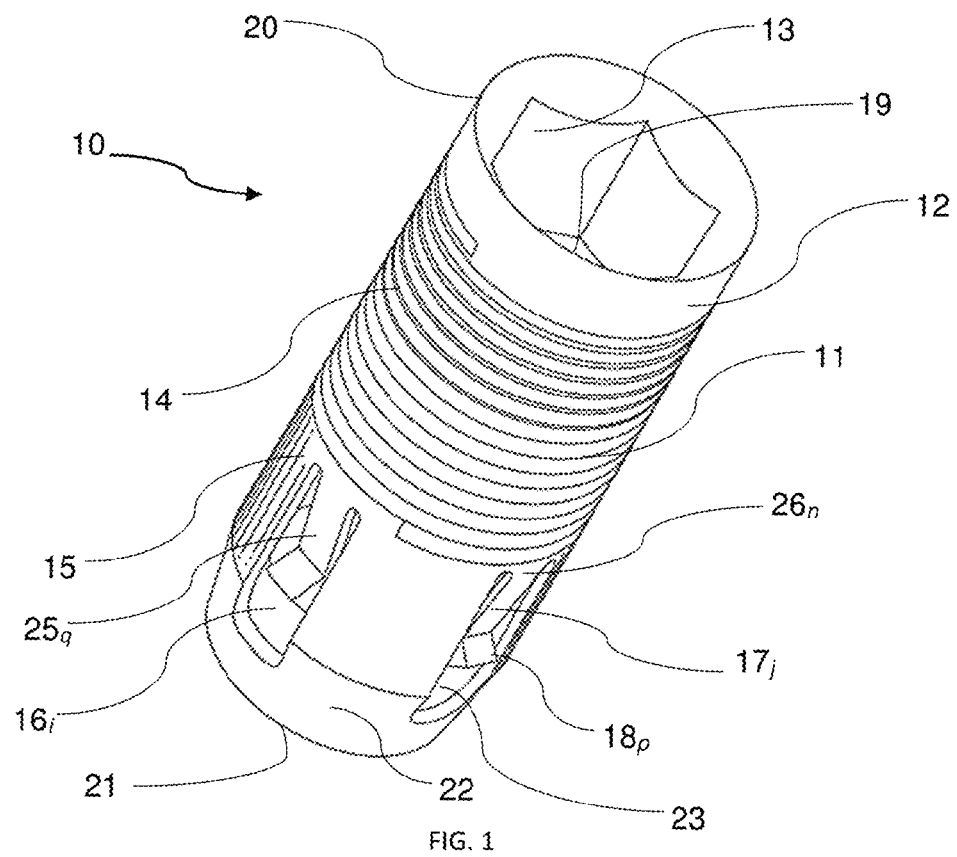
FIG. 1 shows a perspective view of an embodiment of the bladed implant having laterally locking blades in a retracted position.

Before explaining at least one embodiment in detail, it is to be understood that the disclosed technology is not limited in its application to the details of construction and the arrangement of the components set forth in the following description or illustrated in the drawings. The disclosed technology is applicable to other embodiments or of being practiced or carried out in various ways. Also, it is to be understood that the phraseology and terminology employed herein is for the purpose of description and should not be regarded as limiting.

A more complete understanding of the components, processes, assemblies, and methods disclosed herein can be obtained by reference to the accompanying drawings. These figures (also referred to herein as "FIG.") are merely schematic representations (e.g., illustrations) based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 2:
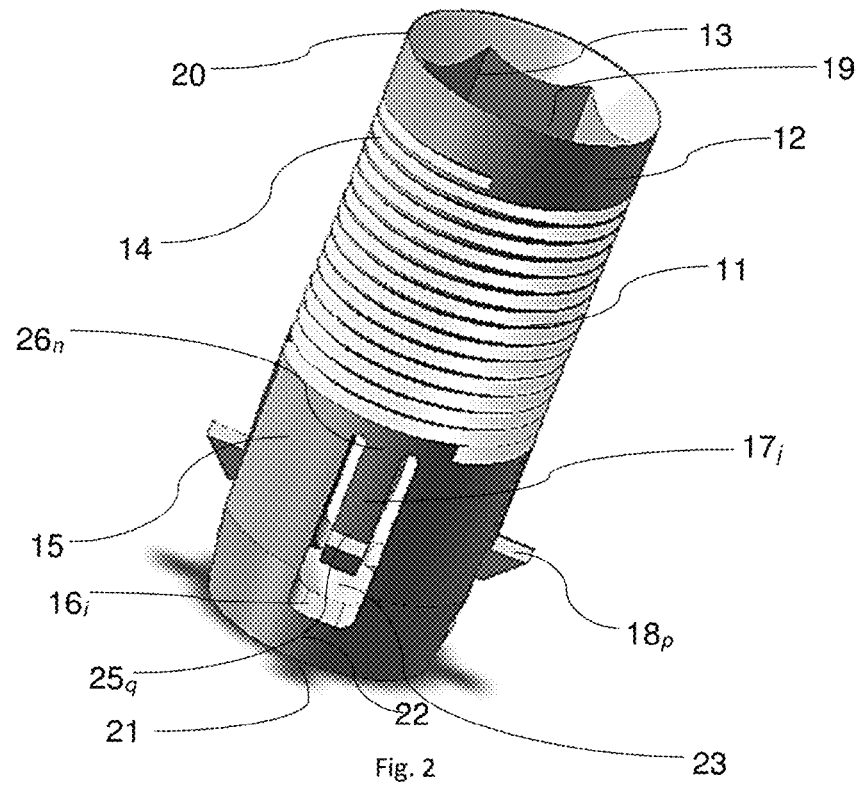
FIG. 2 shows a perspective view of an embodiment of the bladed implant having laterally locking blades in an extended, engaging position.
Figure 7:
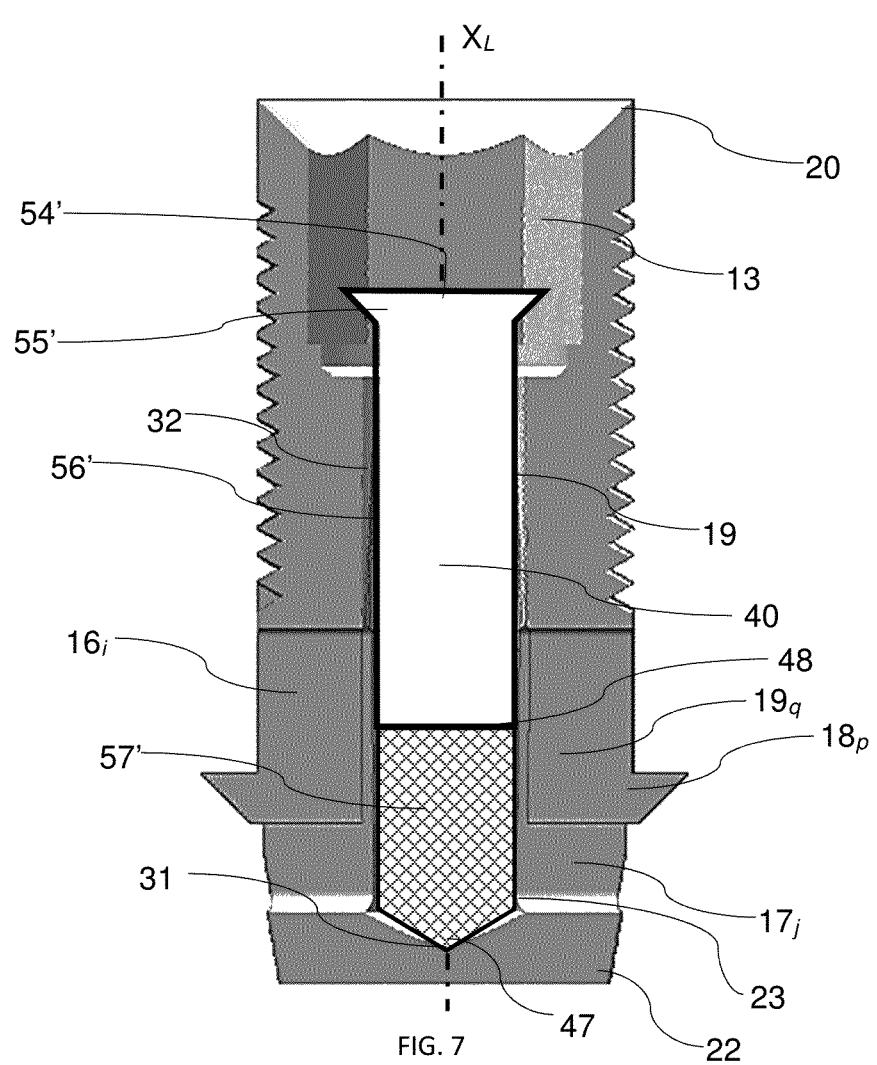
FIG. 7 shows a Y-Z cross section of the implant assembly depicting the actuating shaft

Turning now to FIGS. 1, 2 and 7, where FIG. 1 depicts a perspective view of an embodiment of bladed implant 10 having laterally locking blades in a retracted position. As illustrated, bladed implant assembly 10 for supporting a prosthesis (not shown), the assembly comprising: a monocoque implant body 11 having proximal end 21 and distal end 20 comprising: threaded body portion 14 located at a distal end of monocoque implant 11; abutment portion 12 located distally to threaded body portion 14; non-threaded portion 15 located proximally to threaded body portion 14; conical, or frusto-conical proximal portion 22, located proximally to non-threaded portion 15; and central bore 19 extending through monocoque implant body 11 having distal end and concave proximal end 31 (not shown, see e.g., FIG. 7). As illustrated in FIGS. 1, 2, and 7, central bore 19 can have engagement portion 13 and comprising two or more axially elongated openings 16, radially disposed in non-threaded portion 15 and extending there through with one or more L-shaped resilient blades $25_q$ having elongated distal member $17_j$ and transverse proximal tab $18_p$, elongated distal member 17, extending from the distal end $26_n$ of each of axially elongated openings $16_i$, each elongated distal member $17_j$ of each blade $25_q$ being an integral portion of the external surface of non-threaded body portion 15 and configured to move between a retracted position (See e.g., FIG.

1), whereby each of L-shaped resilient blade(s) $25_q$ radially extends into central bore 19 and an extended position, whereby each of L-shaped resilient blades $25_q$ is flush with the external surface of non-threaded body portion 15 (See e.g., FIG. 2, FIG. 7). As illustrated and shown in FIG. 7, the assembly also comprises shaft member 40 comprising distal portion 56'; and detachable actuating proximal portion 57', wherein actuating proximal portion 57' includes distal end 48 having flat surface and proximal end 47 having arcuate surface, corresponding to the concave surface of proximal end 31 of central bore 19, said shaft member 40 configured to engage central bore 19 thereby causing actuating proximal end 47 to abut against and radially extend one or more of L-shaped resilient blades $25_q$ from non-threaded body portion 15, anchoring monocoque implant 10 into bone structure surrounding monocoque implant 10 located proximally to abutment portion 12.

The term monocoque as used herein refers in an embodiment to a structure in which the outer skin or shell (e.g., of the implant) carries all or most of the torsional and flexural stresses, or, in another embodiment, to a structure in which the body is integral with and shares the stresses with the blades. In other words, a unitary body.

Figure 3A:
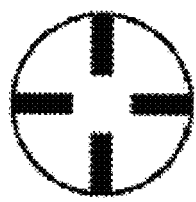
FIG. 3A shows a possible alignment of first row of blades compared to two possible alignments of second row of blades in FIGS. 3B and 3C, according to certain embodiments of the invention.
Figure 3B:
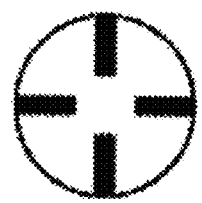
Figure 3B:
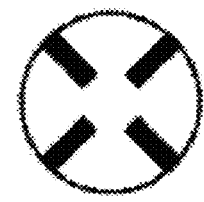

Referring now to an embodiment shown in FIG. 3, in certain embodiments shown of the assemblies described herein, there are optionally four L-shaped blades $25_q$ spaced uniformly about the circumference in non-threaded body portion 15 of monocoque implant body 11, wherein two sets of two blades $25_q$ each are disposed longitudinally in the non-threaded body portion 15, such that one set is closer to proximal end 21. FIG. 3A-3C shows embodiments of the possible spatial relationship between the two sets of blades according to the disclosed technology. In an embodiment, the at least two blades $25_q$ can extend radially at an angle of about 180° with respect to each other.

In certain embodiments of the assemblies described herein, five surfaces of blades $25_q$, optionally may be uniformly spaced about the circumference in the non-threaded portion 15 of internally drilled central bore 19 closer to insertion proximal end 21. The number of blades 25q used in the assemblies and methods described herein, can depend on the application (dental or orthopedic), available bone depth and the like. As illustrated, the sets of blades can be between 2 and 6 at each row, while columns can be aligned or offset. Moreover, the number of blades in each row does not have to be the same, for example, proximal row can have 4 blades, while the distal row can have only 3 or any permutation thereof.

As illustrated in FIG. 7, threads 32 can be formed on surface 23 of central bore 19, extending in an embodiment, from proximal end of threaded portion 14, to proximal end central bore 19 engaging portion 13. The remainder of central bore 19 can remain unthreaded from distal end of non-threaded body portion 15 down to concave proximal end 31 of central bore 19, with concave proximal end 31 diameter slightly smaller than diameter of threads 32. Threads are also formed on surface of threaded body portion 14 of monocoque dental implant 11 extending the whole length of threaded body portion 14. The threads permit monocoque dental implant 11 to be screwed into bore a drilled bore in the bone (not shown). In certain other embodiment, the exterior surface of abutment portion 12 can be cylindrical, square or any other appropriate shape amenable to manipulation.

In an embodiment, central bore 19 further comprises threaded portion 32 and shaft member 40 can be reciprocally threaded (see e.g., 65 FIG. 4B) to threadingly engage the threaded portion 32 of central bore 19 (see e.g., FIG. 7).

The rectangular surface of elongated member $17_j$ can form the outer surface of blade $25_q$ which is resiliently attached to non-threaded body portion 15 of monocoque dental implant 11 at its distal end $26_n$ (FIG. 2, e.g.,) and blade $25_q$ may be resiliently biased on end $26_n$ to move between relaxed retracted position whereby transverse tab $18_p$ is subsumed within central bore 19; and extended position whereby each of L-shaped resilient blade(s) $25_q$ radially extends into central bore 19 and an extended position, whereby each of L-shaped resilient blades $25_q$ is flush with the external surface of non-threaded body portion 15 (See e.g., FIG. 2, FIG. 7). Blades $25_q$ are an integral part of the non-threaded body portion 15 of monocoque implant 11 and at least partially surrounded by openings $16_n$. Openings $16_i$ comprising substantially elongate slots, can also be axially offset at an angle of between 1 and 179 degrees from the longitudinal axis XL (See e.g., FIG. 7) of monocoque body portion 11.

Figure 4A:
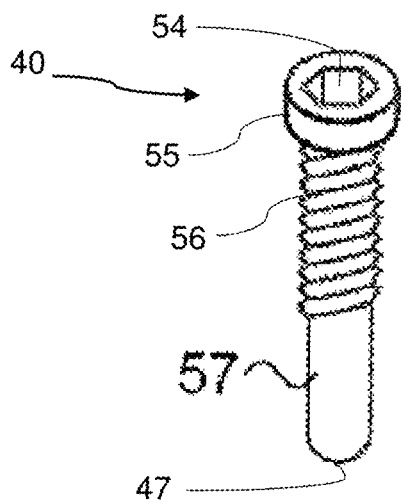
FIGS. 4A, 4B, and 4C show a shaft member with ALLEN™ wrench, PHILIPS™ head, and PHILIPS™ headless distal members of the actuating shaft.
Figure 4B:
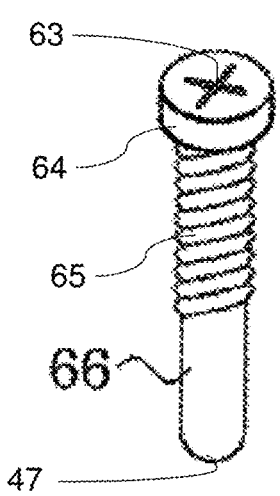
Figure 4C:
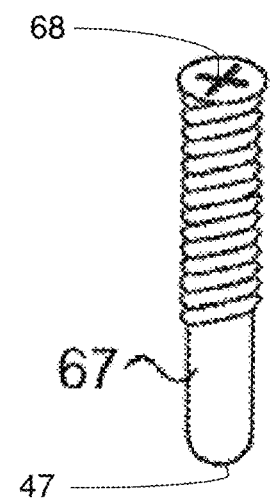

Implant 10 also includes shaft member 40, illustrated in FIGS. 4A-C. Shaft member 40 can comprise an upper portion 55 defining an internal socket 54 adapted to receive a hexagonal, triangular, elliptical or square wrench (not shown). Threads 56 of shaft member 40 can be formed to mate with and engage threads 32 formed on central bore 19 surface. Shaft member 40 can also include detachable lower actuating portion 57 (see e.g., FIG. 4A) with flat surface 48 at the distal end (see e.g., FIG. 7), and an arcuate tip surface at the distal end 47 of detachable actuating lower portion 57. Outer smooth surface of detachable actuating lower portion 57 can be cylindrical, enabling it to slide on inner surface 23 of non-threaded body portion 15 of monocoque implant 11 when actuated by the advance of upper portion 56' of shaft member 40 into the non-threaded body portion 15.

Figures 6A, 6B:
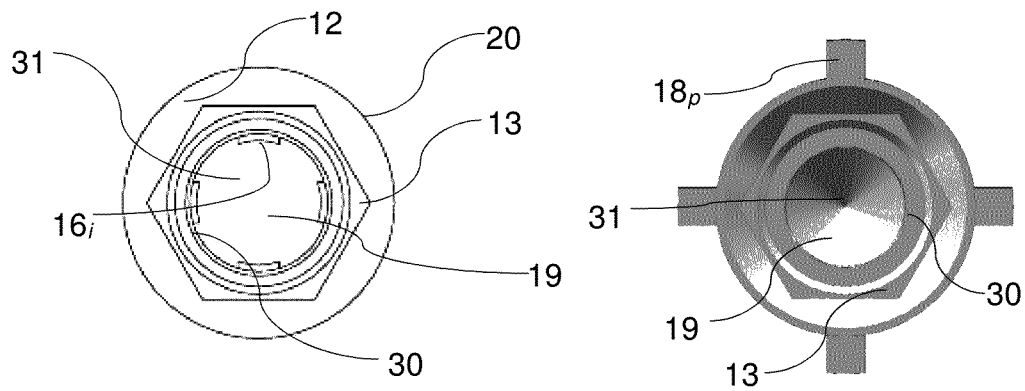
FIG. 6A shows top plan view of the implant with the blade means in a retracted position, with FIG. 6B showing a top plan of the implant with the blade means in the extended position.

As illustrated in FIG. 7, rotation of shaft member 40 within monocoque implant body 11 causes detachable actuating lower portion 57' to abut against internally biased elongated member $17_j$ of blades $25_q$ (See e.g., FIG. 6A) and force transverse tabs $18_p$ of blades $25_q$ to extend radially (See e.g., FIG. 6B), resiliently at point $26_n$, and extend into the surrounding bone. Upon engagement of actuating lower portion 57' of shaft member 40, one or more of transverse tab $18_p$ of L-shaped resilient blades $25_q$ can radially extend to a position of no less than 0.2 millimeter from the external surface of non-threaded body portion 15 (See e.g., FIG. 6B).

Figure 5:
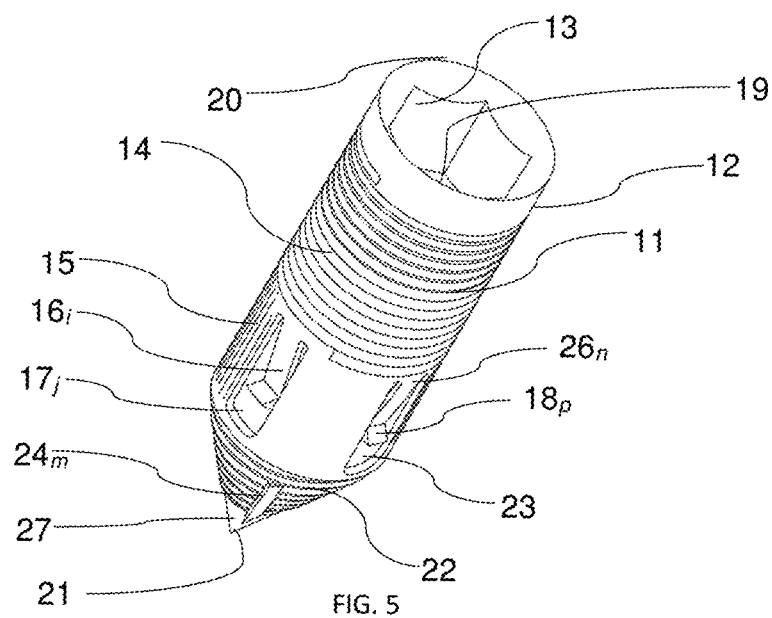
FIG. 5 shows a perspective view of another embodiment of the bladed implant having laterally locking blades in a retracted position.

Turning now to FIG. 5, illustrating a perspective view of another embodiment of the bladed implant 10 having laterally locking blades ($25_q$) in a retracted position. As illustrated, bladed implant 10 having laterally locking blades in a retracted position. As illustrated, bladed implant assembly 10 for supporting a prosthesis (not shown), the assembly comprising: a monocoque implant body 11 having proximal end 21 and distal end 20 comprising: threaded body portion 14 located at a distal end of monocoque implant 11; abutment portion 12 located distally to threaded body portion 14; non-threaded portion 15 located proximally to threaded body portion 14; conical, or frusto-conical proximal portion 22, located proximally to non-threaded portion 15; and central bore 19 extending through monocoque implant body 11 having distal end and concave proximal end 31 (not shown, see e.g., FIG. 7). As illustrated in FIGS. 5, and 7, central bore 19 can have engagement portion 13 and comprising two or more axially elongated openings 16, radially disposed in non-threaded portion 15 and extending there through with one or more L-shaped resilient blades $25_q$ having elongated distal member $17_j$ and transverse proximal tab $18_p$, elongated distal member $17_j$ extending from the distal end $26_n$ of each of axially elongated openings $16_n$ each elongated distal member $17_j$ of each blade $25_q$ being an integral portion of the external surface of non-threaded body portion 15 and configured to move between a retracted position (See e.g., FIG. 5), whereby each of L-shaped resilient blade(s) $25_q$ radially extends into central bore 19 and an extended position, whereby each of L-shaped resilient blades $25_q$ is flush with the external surface of non-threaded body portion 15. As also illustrated, proximal end portion 22 of monocoque implant 11 can be threaded cone thus facilitating penetration into the subject bone. Furthermore, proximal end portion 22, can further comprise plurality of notches $24_m$ disposed on the lateral surface of the threaded cone forming proximal end portion 22 of monocoque implant 11, with apex of the threaded conical proximal end 22 is razor edged 27, such that monocoque implant 11 can be threaded into a bore drilled into the patient bone.

As suggested by FIG. 7, arcuate proximal end 47 of detachable actuating lower portion 57' is inserted into central bore 19 and detachable actuating lower portion 47 slides into position, making contact with concave proximal end 31 of non-threaded portion of central bore 19, causing detachable actuating lower portion 57' to abut against internally biased elongated member $17_j$ of blades $25_q$ and force transverse tabs $18_p$ of blades $25_q$ to extend radially, resiliently at point $26_n$, and extend into the surrounding bone. Thereafter, upper portion 56' can be removed by reversibly threading upper portion 56'.

In a still further embodiment upper portion shaft member 40 and detachable actuating lower portion 57' (see e.g., FIG. 7) can be combined into a single special blade actuation ALLEN™ screw 57 shown in FIG. 4A or a special blade actuation headed PHILIPS™ 66 or headless PHILIPS™ screw 67, shown respectively in Figured 4B and 4C. In certain embodiments shaft member 40 is a single member wherein portions 57, 66 and 67 respectively can be continuous and are threaded.

The authors have additionally, discovered that in the event that should the expanding dental implants, exemplified by U.S. Pat. No. 6,332,778 (Choung), require removal, it is often necessary to utilize a trephine having sufficient diameter to surround the deformed implant ends. The result of trephine removal is a cylindrical bone core that leaves a bone defect that may be refractive to implant replacement.

Moreover, the central bore can be configured to operate as a reservoir for therapeutically effective substances, which can be configured to be expelled from the central bore upon insertion of the shaft member, either by threading it, or in another embodiment, by using the non-detachable shaft members illustrated for example in FIG. 4, as plungers of the actuating lower portion. As illustrated on FIG. 4C, it is possible to use a headless PHILIPS screw head, which can be configured to be inserted into central bore such that it acts as a hypodermic plunger acting against the substance residing in concave proximal portion 31 of central bore 19 (see e.g., FIGS. 6B, 7). The substance can be in a capsule that can release the material inside, for example, a liquid, gel, powder or the like, and may comprise an antibiotic, an analgesic, a medicament, stem cells or a composition comprising one or more of the foregoing. Additionally or alternatively, no capsule is present and the therapeutically effective substance or composition is in the form of a gel.

As indicated above, in certain embodiments, shaft member 40 upper portion 56 does not contain any external threading and is configured to be slidably, frictionally coupled to central bore 19.

Of course, the present disclosed technology is not intended to be restricted to any particular form or arrangement, or any specific embodiment disclosed in this document, or any specific use, since the same may be modified in various particulars or relations without departing from the spirit or scope of the claimed disclosed technology as shown above and described of which the assembly shown is intended only for illustration and for disclosure of an operative embodiment and not to show all of the various forms or modifications in which the present disclosed technology might be embodied or operated.

In the above description, an embodiment is but an example or implementation of the disclosed technology. The various appearances of phrases like "one embodiment", "an embodiment", or "certain embodiments of the assemblies described herein", do not necessarily all refer to the same embodiments.

Although various features of the disclosed technology may be described in the context of a single embodiment, the features may also be provided separately or in any suitable combination. Conversely, although the disclosed technology may be described herein in the context of separate embodiments for clarity, the disclosed technology may also be implemented in a single embodiment.

Reference in the specification to "certain embodiments of the assemblies described herein", "an embodiment", "one embodiment", or "other embodiments" means that a particular feature, structure, or characteristic described in connection with the embodiments is included in at least certain embodiments of the assemblies described herein, but not necessarily all embodiments, of the disclosed technology s.

It is to be understood that the phraseology and terminology employed herein is not to be construed as limiting and are for descriptive purpose only.

The principles and uses of the teachings of the present disclosed technology may be better understood with reference to the accompanying description, figures, and examples.

It is to be understood that the details set forth herein do not construe a limitation to an application of the disclosed technology.

Furthermore, it is to be understood that the disclosed technology can be carried out or practiced in various ways and that the disclosed technology can be implemented in embodiments other than the ones outlined in the description above.

It is to be understood that the terms "including", "comprising", "consisting", and grammatical variants thereof do not preclude the addition of one or more components, features, steps, or integers or groups thereof and that the terms are to be construed as specifying components, features, steps, or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can", or "could" be included, that particular component, feature, structure, or characteristic is not required to be included.

Where applicable, although state diagrams, flow diagrams or both may be used to describe embodiments, the disclosed technology is not limited to those diagrams or to the corresponding descriptions. For example, flow need not move through each illustrated box or state, or in exactly the same order as illustrated and described.

Methods of the present disclosed technology may be implemented by performing or completing manually, automatically, or a combination thereof, selected steps or tasks.

The term "method" may refer to manners, means, techniques, and procedures for accomplishing a given task including, but not limited to, those manners, means, techniques, and procedures either known to, or readily developed from known manners, means, techniques, and procedures by practitioners of the art to which the disclosed technology belongs.

In addition, for the purposes of the present disclosure, directional or positional terms such as "Proximal", "Distal", "top", "bottom", "upper," "lower," "side," "front," "frontal," "forward," "rear," "rearward," "back," "trailing," "above," "below," "left," "right," "radial," "vertical," "upward," "downward," "outer," "inner," "exterior," "interior," "intermediate," etc., are merely used for convenience in describing the various embodiments of the present disclosure.

The descriptions, examples, methods, and materials presented in the claims and the specification are not to be construed as limiting, but rather as illustrative only.

Meanings of technical and scientific terms used herein are to be commonly understood as by one of ordinary skill in the art to which the disclosed technology belongs, unless otherwise defined.

The present disclosed technology may be implemented in the testing or practice with methods and materials equivalent or similar to those described herein.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of certain embodiments of the assemblies described herein shall not be construed as an admission that such reference is available as prior art to the present disclosed technology.

While the disclosed technology has been described with respect to a limited number of embodiments, these should not be construed as limitations on the scope of the disclosed technology, but rather as exemplifications of some of the preferred embodiments. Other possible variations, modifications, and applications are also within the scope of the disclosed technology. Accordingly, the scope of the disclosed technology should not be limited by what has thus far been described, but by the appended claims and their legal equivalents.

What is claimed is:

1. A bladed implant assembly for supporting a prosthesis, the assembly comprising:
   a. a monocoque implant having a proximal end and a distal end comprising:
      i. a threaded body portion located at a distal end of the monocoque implant;
      ii. an abutment portion located distally to the body portion;
      iii. a non-threaded portion located proximally to the threaded body portion;
      iv. a conical, or frusto-conical proximal end, located proximally to the non-threaded portion; and
      v. a central bore extending through the monocoque implant body having a distal end and a concave proximal end, having an engagement portion and comprising two or more axially elongated openings radially disposed and extending through the non-threaded portion with one or more L-shaped resilient blades having an elongated distal member and a transverse proximal tab, the elongated distal member extending from the distal end of the axially elongated openings, each elongated distal member of each blade being a portion of the external surface of the non-threaded body portion and configured to move between a retracted position, whereby each of the L-shaped resilient blades radially extends into the central bore and an extended position, whereby each of the L-shaped resilient blades is flush with the external surface of the non-threaded body portion; and
   b. a shaft member comprising:
      i. a distal portion; and
      ii. a detachable actuating proximal portion, wherein the actuating proximal portion includes a distal end having a flat surface and a proximal end having arcuate surface, corresponding to the concave surface of the proximal end of the central bore, said shaft member configured to engage the central bore thereby causing the actuating lower portion to radially extend one or more of each of the L-shaped resilient blades from the non-threaded body portion, anchoring the monocoque implant into bone structure surrounding the monocoque implant located proximally to the abutment portion.

2. The implant of claim 1, wherein the central bore further comprises threaded portion and the shaft member is reciprocally threaded to threadingly engage the threaded central bore.

3. The assembly according to claim 2, wherein the one or more openings comprising substantially elongate slots, are offset at an angle of between 1 and 179 degrees from the longitudinal axis of the body portion.

4. The assembly according to claim 3, wherein the one or more blades comprise at least two blades that extend radially on a common plane.

5. The assembly according to claim 4, wherein the at least two blades extend radially at an angle of about 180° with respect to each other.

6. The assembly according to claim 5, comprising at least two sets of blades, a first set disposed at a proximal section of the non-threaded body portion and at least a second set disposed at a distal section of the non-threaded body portion.

7. The assembly according to claim 1, wherein upon engagement of the actuating portion of the shaft member, one or more of the transverse tab of the L-shaped resilient blades radially extend to a position of no less than 0.2 millimeter from the external surface of the non-threaded body portion.

8. The assembly of claim 1, wherein the frusto-conical proximal end is non-threaded.

9. The assembly of claim 1, wherein the conical proximal end is threaded.

10. The assembly of claim 9, wherein the threaded conical proximal end further comprise a plurality of notches disposed on the lateral surface of the threaded cone.

11. The assembly of claim 10, wherein the apex of the threaded conical proximal end is razor edged.

12. The assembly of claim 1, wherein the central bore further comprising therapeutically effective substance, configured to be expelled upon actuation of the one or more of the L-shaped resilient blades from the non-threaded body portion.

13. The assembly of claim 12, wherein the substance comprising an antibiotic, an analgesic, a medicament, stem cells or a composition comprising one or more of the foregoing.

* * * * *